United States Patent [19]

Kesler

[11] 4,115,471

[45] Sep. 19, 1978

[54] METHOD FOR SEPARATING THE PRODUCT EFFLUENT OF AN ALKYLATION PROCESS

[75] Inventor: Michael G. Kesler, East Brunswick, N.J.

[73] Assignee: Mobil Oil Corporation, New York, N.Y.

[21] Appl. No.: 825,747

[22] Filed: Aug. 18, 1977

[51] Int. Cl.² .............................................. C07C 3/54
[52] U.S. Cl. ................... 260/683.43; 203/27; 203/23; 203/78; 203/88; 260/683.48; 260/683.58; 260/683.62
[58] Field of Search ............... 260/683.43, 683.48, 260/683.58, 683.62; 203/23, 27, 78, 88

[56] References Cited

U.S. PATENT DOCUMENTS

| | | | |
|---|---|---|---|
| 3,233,007 | 2/1966 | Chapman | 260/683.58 |
| 3,723,565 | 3/1973 | Henderson | 260/683.43 |
| 3,919,342 | 11/1975 | Chapman | 260/683.48 |

Primary Examiner—Delbert E. Gantz
Assistant Examiner—C. E. Spresser
Attorney, Agent, or Firm—Charles A. Huggett; Carl D. Farnsworth

[57] ABSTRACT

In an alkylation process, the separation of the hydrocarbon effluent is accomplished by modifying the depropanizer tower to provide a lower bottom temperature. The depropanizer bottoms is flash separated to release an isobutane rich recycle stream with higher boiling alkylate being passed to an isostripper for separation with alkylation hydrocarbon effluent not passing through the above sequence. The use of low pressure steam for heat duty in the above sequence reduces energy requirements of the processing combination.

7 Claims, 1 Drawing Figure

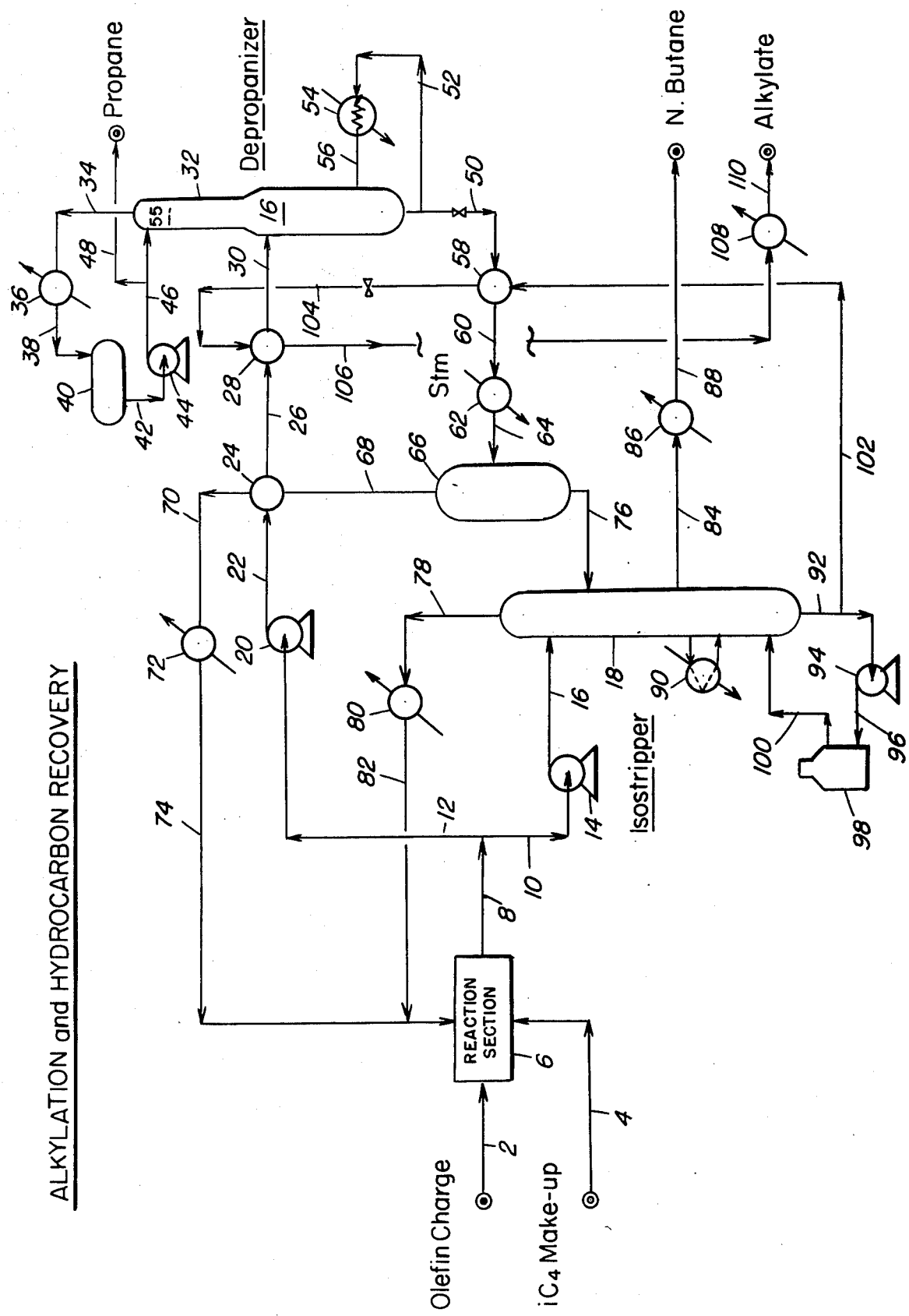

METHOD FOR SEPARATING THE PRODUCT EFFLUENT OF AN ALKYLATION PROCESS

BACKGROUND OF THE INVENTION

The alkylation of isoparaffins with olefins using acid acting catalysts, such as hydrogen fluoride, sulfuric acid, and other catalysts of the prior art is of commercial importance in producing relatively high octane motor fuel components. The isoparaffin normally used is isobutane, which is generally reacted with a mixture of butene isomers or a mixture of propylene and butene isomers to provide a reaction product comprising longer chain isoparaffins comprising $C_5 - C_9$ isoparaffins. The $C_5$ and heavier products of the reaction are termed alkylate. In a typical alkylation process, the effluent from an alkylation reactor comprising catalyst, unconsumed reactants and alkylate is passed through a separator system, thereby forming a catalyst phase and a hydrocarbon effluent phase. The separated catalyst phase is generally returned directly to the reactor or it may be treated to remove water therefrom if warranted. The hydrocarbon phase thus separated is further processed in a sequence of steps to separate desired alkylate product from other hydrocarbons and particularly those comprising unconsumed reactant materials. Since the reaction between an isoparaffin and an olefin in an alkylation process is effected with a large molar excess of isoparaffin, the hydrocarbon effluent phase contains relatively large amounts of unreacted isoparaffins which must be efficiently and economically recovered for recycle to the alkylation reaction zone. In addition, propane charged to or produced in the alkylation zone must be economically separated in order to minimize undesired build-up of this material as well as that of normal butane. The process combination of the present invention is particularly concerned with improving the operating efficiency and economics of separating the hydrocarbon effluent of an alkylation process to achieve the herein desired results.

SUMMARY OF THE INVENTION

The present invention relates to a method and arrangement of processing steps for separating particularly the hydrocarbon effluent stream of an alkylation reaction zone. More particularly, the invention relates to the method and sequence of separation steps providing a major energy conservation during the recovery of desired product and from recycle reactant materials. In a more particular embodiment, the depropanizer tower of an alkylation process is modified to eliminate a sidestream withdrawal so that a lower tower bottom temperature may be achieved. In this embodiment, the depropanizer tower bottom stream is flash separated under selected temperature and pressure conditions promoting particularly the release of light ends including isobutane recycle material. The bottoms from the flash step is processed in an isostripper vessel or separation zone with a portion of the alkylation reaction zone separated hydrocarbon product effluent stream. In such an operation, it has been found possible to reduce the overall energy consumption by approximately 20 million BTU/Hr.

The processing sequence of the present invention can be relied upon to reduce the energy requirements of the process either directly by a reduction in the total process heat required and indirectly by lowering the pressure of steam used in the process. A reduction in the depropanizer tower size, its bottom operating temperature and its related retort and condenser duties can also be achieved. The lowering of the depropanizer bottoms temperature permits the use of low pressure steam in place of higher pressure steam thereby substantially reducing the overall heat requirements of the process. It is also to be recognized that the flash separator temperature and pressure conditions are trimmed to obtain and maintain an isobutane recycle purity of about 80% and such an operation in this processing sequence further contributes to energy conservation. The operating sequence of the present invention can be used with advantage in revamping an existing operation with a minimum disturbance of available equipment.

The drawing is a diagrammatic sketch in elevation of the processing sequence of the present invention directed to separating the product effluent of an alkylation process such as an HF alkylation process.

Referring now to the drawing by way of example, an olefin charge comprising a mixture of $C_3 - C_4$ olefins is charged to the process by conduit 2. A fresh make-up isobutane rich stream is charged to the process by conduit 4. The reactants thus charged with recycle isobutane rich material in conduit 74 pass to a reaction zone 6 under conditions providing an isobutane to olefin ratio in the range of 5:1 to 20:1 and more usually about 10 or 12 to 1. In alkylation zone 6, the reaction of an olefin with an isoparaffin is particularly promoted to produce larger chain isoparaffins. Sulfuric acid and hydrogen flouride, the two most important alkylation catalysts of the day are used to alkylate isobutane with propane and butenes particularly. The reaction is highly exothermic and competes with polymerization of olefins. Thus, a substantial excess of isobutane is normally provided to particularly promote the desired alkylation reaction. Alkylation reaction conditions of temperature, pressure, isobutane/olefin ratio and catalyst to hydrocarbon ratio are maintained within limits of the prior art. The alkylation of isobutane with propylene, butylenes and amylenes can be effected at temperatures within the range of 0° F to about 200° F and preferably between about 50° F and about 125° F; at pressures sufficiently high to maintain the reactants and catalysts employed as liquids. The isobutane to olefin mole ratio may be in the range of 5:1 and about 20:1; but preferably less than about 15:1 is employed. In the particular arrangement of the drawing, it is contemplated employing hydrogen fluoride (HF) as the liquid phase catalyst and preferably this catalyst should contain less than about 5 weight percent water and comprise at least about 65 weight percent of titratable acid. Since the recovery of acid catalyst from the hydrocarbon effluent is not a part of the present invention, it is to be recognized that such separation may follow any one of the desired techniques of the prior art. The present invention is particularly concerned with the separation of the hydrocarbon effluent after recovery from the acid catalyst phase.

Referring now to the drawing, the hydrocarbon effluent of the alkylation operation is removed by conduit 8 at a temperature of about 115° F in this specific arrangement and divided into two streams 10 and 12. Stream 10 comprising about 84800 B/D (barrels per day) of alkylate hydrocarbon effluent in this specific embodiment is passed by pump 14 and conduit 16 to an upper portion of isostripper tower 18. A smaller portion of the separated alkylate hydrocarbon effluent and amounting to about 70660 B/D is conveyed by conduit 12 to pump 20 and conduit 22 to heat exchanger 24 wherein the temperature of this alkylate stream is raised to about 154° F. The alkylate stream thus heated is then passed by conduit 26 to heat exchanger 28 wherein its temperature is further raised to about 170° F before passage by conduit 30 to a lower intermediate portion of depropanizer tower 32. That is, in a 55 tray tower of smaller diameter in an upper portion than in a lower portion, the alkylate stream in conduit 30 is charged to an upper part of the largest diameter portion of the tower, generally about the 16th tray.

In depropanizer tower 32, an overhead comprising $C_3$ and lighter materials is withdrawn by conduit 34, cooled in cooler 36 to a temperature of about 132° F before passage by conduit 38 to surge drum 40 maintained at a pressure of about 270 psig. The recovered propane rich product in drum 40 is passed by conduit 42 to pump 44 and thence a portion thereof by conduit 46 as reflux to the top of tower 32. Propane rich gas in excess of that recycled to tower 32 is withdrawn by conduit 48.

An alkylate product separated in tower 32 and comprising primarily $C_4$ and higher boiling material is withdrawn from the bottom of tower 32 at a temperature of about 232° F by conduit 50. A portion of this withdrawn material is passed by conduit 52 as reboiler liquid to heat exchanger 54 relying on 40 psig steam to provide about 50 million BTU of heat to the liquid recycled to the bottom of tower 32 by conduit 56. Liquid alkylate withdrawn by conduit 50 is passed to heat exchanger 58 wherein the temperature of the liquid is reduced to about 180° F before passage by conduit 60 to heater 62 and thence by conduit 64 to flash separator 66. Flash separator 66 is maintained at a temperature of about 181° F and a pressure of about 135 psig. A separation is made in separator 66 particularly promoting the recovery of an isobutane rich steam for recycle to the alkylation reaction zone and withdrawn by conduit 68. This flash separated isobutane rich stream will contain up to about 11 volume percent of $C_3$ hydrocarbons, a small amount of $C_5$ plus material usually not substantially above about 1.5 volume percent and about 80 volume percent of isobutane. Some normal butane will also be found in this recycle stream. The isobutane rich stream in conduit 68 is passed to heat exchanger 24 wherein its temperature is reduced to about 154° F before passage by conduit 70 to cooler 72 wherein the temperature of the isobutane rich recycle is further reduced to about 105° F. The cooled recycled isobutane rich stream is passed by conduit 74 to the alkylation reaction zone 6.

The liquid alkylate product separated in flash zone 66 and comprising $C_5$ and higher boiling alkylate product material is passed by conduit 76 to an upper portion of isostripper tower 18. In the isostripper tower, an isobutane rich recycle stream is recovered and withdrawn from the top thereof by conduit 78, cooled in cooler 80 to a temperature of about 105° F before being recycled by conduit 82 to the alkylation zone 6.

In the isostripper tower 18 a separation of the alkylate product effluent charged thereto by conduits 16 and 76 is made to recover normal butane at a temperature of about 185° F withdrawn therefrom by conduit 84 which material is then passed through cooler 86 effecting a temperature reduction of the recovered normal butane to about 105° F. A low pressure steam heat exchanger 90 provides heat in a pump around stream withdrawn from tower 18. Alkylate product is withdrawn from the bottom of tower 18 by conduit 92 at an elevated temperature of about 389° F. A portion of this withdrawn alkylate product is passed to pump 94 and then by conduit 96 to a furnace 98 wherein its temperature is raised to about 400° F before recycle by conduit 100 as reboiler liquid to the bottom portion of tower 18. Alkylate product not used as reboiler fluid is withdrawn by conduit 102 for passage to heat exchanger 58 wherein the alkylate is temperature reduced to about 240° F. The alkylate thus temperature reduced is passed by conduit 104 to heat exchanger 28 wherein its temperature is further reduced to about 174° F. The cooled alkylate product is passed from heat exchanger 28 by conduit 106 to cooler 108 wherein a further temperature reduction is effected to permit the withdrawal of alkylate product of the process at a temperature of about 105° F by conduit 110.

It is to be particularly noted that low pressure steam, of about 40 psig, is relied upon to supply a substantial portion of the process heat beyond that provided by furnace 98 and this use of low pressure steam contributes significantly to a reduction in overall energy requirements of the process.

Having thus generally described the invention to which the present is directed and provided a specific embodiment in support thereof, it is to be understood that no undue restrictions are to be imposed by reason thereof.

I claim:

1. In a process for alkylating isoparaffins and olefins with an acid catalyst, the improved method for separating the hydrocarbon effluent of the alkylation process which comprises, separating the hydrocarbon effluent of an alkylation process into first and second separate hydrocarbon effluent streams of the same composition, passing the first of said hydrocarbon effluent streams to a stripping zone maintained under temperature and pressure conditions providing the recovery of an isoparaffin rich stream from the upper portion thereof and a product alkylate stream from a bottom portion thereof, passing the second of said hydrocarbon effluent streams after cooling to a depropanizer separation zone, recovering propane and lower boiling components from said depropanizer zone separate from higher boiling alkylate effluent material, passing separated higher boiling alkylate effluent material from said depropanizer zone to a flash zone maintained under temperature and pressure conditions providing an isoparaffin rich stream separate from a higher boiling alkylate product stream, recycling the isoparaffin rich stream separated in said flash zone after cooling thereof to said alkylation zone, and passing the higher boiling alkylate product stream separated in said flash zone to said stripping zone.

2. The process of claim 1 wherein the isoparaffin rich stream separated from said flash zone is passed in indirect heat exchange with said second hydrocarbon effluent stream before further cooling and recycle to said alkylation zone.

3. The process of claim 1 wherein alkylate product separated from said stripping zone is passed in indirect heat exchange with material passed to said flash zone and said depropanizer zone to reduce its temperature before withdrawal from the process.

4. The process of claim 1 wherein a normal butane rich stream is recovered from said stripping zone.

5. The process of claim 1 wherein low pressure steam is relied upon to provide heat indirectly to the bottom portion of the depropanizer zone and to preheat the material charged to the flash zone.

6. The process of claim 1 wherein alkylate product withdrawn from said stripping zone is heated in a furnace zone and returned to a bottom portion of said stripping zone.

7. The process of claim 6 wherein a portion of the heat supplied to said stripping zone is supplied to a pump around stream by low pressure steam.

* * * * *